US008415398B2

(12) United States Patent
Liang et al.

(10) Patent No.: US 8,415,398 B2
(45) Date of Patent: Apr. 9, 2013

(54) MATERIALS AND METHODS FOR TREATING VIRAL INFECTIONS

(75) Inventors: Hao Yi Liang, Guangzhou (CN); Francis Chi, Kowloon (HK); Qingfu Xu, Rochester, NY (US); Bill Piu Chan, Beijing (CN)

(73) Assignee: Obio Pharmaceutical (H.K.) Limited, Hong Kong (CN)

( * ) Notice: Subject to any disclaimer, the term of this patent is extended or adjusted under 35 U.S.C. 154(b) by 1175 days.

(21) Appl. No.: 11/605,551

(22) Filed: Nov. 28, 2006

(65) Prior Publication Data

US 2007/0135525 A1 Jun. 14, 2007

Related U.S. Application Data

(60) Provisional application No. 60/740,584, filed on Nov. 28, 2005, provisional application No. 60/810,773, filed on Jun. 2, 2006, provisional application No. 60/818,885, filed on Jul. 6, 2006, provisional application No. 60/847,020, filed on Sep. 25, 2006.

(51) Int. Cl.
*A61K 31/13* (2006.01)
*A61K 31/16* (2006.01)

(52) U.S. Cl. ................................ 514/665; 514/613

(58) Field of Classification Search .................. 514/665, 514/613
See application file for complete search history.

(56) References Cited

U.S. PATENT DOCUMENTS

| | | | |
|---|---|---|---|
| 3,991,190 A | 11/1976 | Garzia et al. | |
| 5,243,036 A | 9/1993 | Ranieri et al. | |
| 5,292,773 A | 3/1994 | Hirsch et al. | |
| 5,314,917 A | 5/1994 | Michaels et al. | |
| 5,430,064 A | 7/1995 | Hirsch et al. | |
| 5,554,655 A | 9/1996 | Thoene | |
| 5,576,351 A | 11/1996 | Yoshimura et al. | |
| 5,646,189 A * | 7/1997 | Thoene | 514/665 |
| 5,686,436 A | 11/1997 | Van Dyke | |
| 5,725,870 A | 3/1998 | Thoene | |
| 5,846,961 A | 12/1998 | Van Dyke | |
| 6,063,383 A | 5/2000 | Hsu et al. | |
| 6,514,955 B1 | 2/2003 | Van Dyke | |
| 2004/0106591 A1 | 6/2004 | Pacioretty et al. | |
| 2004/0157783 A1 | 8/2004 | McCaddon | |
| 2005/0014717 A1 | 1/2005 | Locniskar et al. | |
| 2005/0051103 A1 | 3/2005 | Chi et al. | |
| 2006/0173078 A1 | 8/2006 | McGregor | |
| 2006/0211748 A1 | 9/2006 | Bain et al. | |
| 2007/0031510 A1 * | 2/2007 | Flavin-Koenig | 424/643 |

FOREIGN PATENT DOCUMENTS

| | | |
|---|---|---|
| DE | 41 03 177 | 8/1992 |
| DE | 198 17 511 | 10/1999 |
| EP | 0 491 643 | 6/1992 |
| RU | 2175230 | 10/2001 |
| WO | WO 92/13863 | 8/1992 |
| WO | WO 93/06832 | 4/1993 |
| WO | WO 9949860 A1 * | 10/1999 |
| WO | WO 2005023240 A2 * | 3/2005 |

OTHER PUBLICATIONS

Anderson et al., "Characterization of Cysteamine as a Potential Contraceptive Anti-HIV agent," *J. Andrology*, Jan./Feb. 1998, vol. 19, No. 1, pp. 37-49.
Bergamini et al., "Cystamine Potently Suppresses In Vitro HIV Replication in Acutely and Chronically Infected Human Cells," *J. Clin. Invest.*, May 1994, vol. 93, pp. 2251-2257.
Bergamini et al, "In Vitro Inhibition of the Replication of Human Immunodeficiency Virus Type 1 by β- Mercaptoethylamine (Cysteamine)," *J. Infectious Diseases*, 1996, vol. 174, pp. 214-218.
Braun et al., "Effect of the sulfhydryl compound cystemaine on gamma-radiation-induced mutations in double-stranded M13 DNA," *Mutat. Res.*, 1996, vol. 364, No. 3, pp. 171-182.
Dulis et al, "Serum alkaline phosphatase isoenzymes in lymphoproliferative diseases," *Cancer Research*, Aug. 1978, vol. 38, pp. 2519-2522.
Gutschow et al., "Bis((2,4-dioxo-1,2,3,4-tetrahydroquinazolin-3-yl)alkyl) disulfane and 3-(mercaptoalkyl)quinazolin-2,4(1H,3H)-dione: synthesis by ring transformation and antiviral activity. 42. Heterocyclic azines with heteroatoms in the 1- and 3- positions," *Pharmazie*, Oct. 1995, vol. 50, No. 10, pp. 672-675, Abstract Only.
Huang, "Inhibition of Initiation of Bacteriophage T4 DNA Replication by Perturbation of *Escherichia coli* Host Membrane Composition," *J. Virology*, Dec. 1979, vol. 32, No. 3, pp. 917-924.
Limoli et al., "DNA damage in bromodeoxyuridine substituted SV40 DNA and minichromosomes following UVA irradiation in the presence of Hoechst dye 33258," *Int. J. Radiat. Biol.*, 1994, vol. 66, No. 6, pp. 717-728.
McDonnell et al., "Zinc Ejection as a New Rationale for the Use of Cystamine and Related Disulfide-Containing Antiviral Agents in the Treatment of AIDS," *J. Med. Chem.*, 1997, vol. 40, pp. 1969-1976.
Neumann et al, "Comparative study of alkaline phosphatase activity in lymphocytes, mitogen-induced blasts, lymphoblastoid cell lines, acute myeloid leukemia, and chronic lymphatic leukemia cells," *Proc. Nat'l Acad. Sci.*, 1976, vol. 73, No. 5, pp. 1432-1436.
Thoene, "In vitro effectiveness of aminothiols and disulfides against HIV-1," *Clinical Research*, 1992, vol. 40, No. 2, pp. 246A.
Yang et al., "Effects of Cysteamine on Growth Performance, Digestive Enzyme Activities, and Metabolic Hormones in Broilers," *Poultry Science*, 2006, vol. 85, pp. 1912-1916.
Golohvastova, E.L. "Clinic and treatment of hiv infection"*Lechahiy vrach*, 2001, retrieved from http://www.Ivrach/2001/01/4528452?p=2.
Akobyan of al. "Genital herpes: Contemporary problems and ways of their solutions" *Clinic Microbiology and antimicrobial chemotherapy*, 2001, pp. 4-18, vol. 5, No. 1.

* cited by examiner

*Primary Examiner* — Shengjun Wang
(74) *Attorney, Agent, or Firm* — Saliwanchik, Lloyd & Eisenschenk

(57) ABSTRACT

The subject invention provides materials and methods for treating various health conditions, including the prevention and/or treatment of a viral infection. In a preferred embodiment, a cysteamine compound is administered to a subject to treat an influenza virus infection. More preferably, a cysteamine compound is administered to a subject to treat influenza A, influenza B, influenza C virus infections, including avian influenza virus subtypes (such as H5N1 avian influenza virus).

14 Claims, 2 Drawing Sheets

MATERIALS AND METHODS FOR TREATING VIRAL INFECTIONS

CROSS-REFERENCE TO A RELATED APPLICATION

This application claims the benefit of U.S. Provisional Application Ser. No. 60/740,584, filed Nov. 28, 2005; Ser. No. 60/810,773, filed Jun. 2, 2006; Ser. No. 60/818,885, filed Jul. 6, 2006; and Ser. No. 60/847,020, filed Sep. 25, 2006, all of which are hereby incorporated by reference in their entirety, including any figures and/or tables.

BACKGROUND OF THE INVENTION

A virus is a small parasite consisting of nucleic acid (RNA or DNA) enclosed in a protein coat. Viruses can only replicate by infecting a susceptible host cell and directing the host cell machinery to produce more viruses. Glycoproteins (located in the protein coat) mediate the adsorption to, and the penetration of, the virus into susceptible host cells.

Most viruses are classified into broad categories based on the types of nucleic acids formed during replication and the pathway by which mRNA is produced. In general, viruses have either RNA or DNA as their genetic material, wherein the nucleic acid can be single- or double-stranded.

Important virus families of the DNA type (also classified as Classes I and II viruses—See Harvey, L. et al., *Molecular Cell Biology*, Fourth Edition, W. H. Freeman and Company (2000)) include adenoviridae, herpesviridae, poxviridae, papovaviridae, densovirinae, and parvovirinae. Virus families typically classified of the RNA type (also classified as Classes III-VI, See *Molecular Cell Biology*) include bimaviridae, reoviridae, astoviridae, arterivirus, caliciviridae, coronaviridae, flaviviridae, picomaviridae, togaviridae, polioviruses, bomaviridae, filoviridae, paramyxovirinae, pneumovirinae, rhabdoviridae, bunyaviridae, and orthomyxoviridae.

Influenza, commonly known as the "flu," is a contagious disease that is caused by the influenza virus, classified in the orthomyxoviridae family. There are three known influenza-type viruses which affect human beings: Influenza A, B and C. Influenza A viruses have been isolated from many animal species in addition to humans, while the influenza B and C viruses have been found to infect mainly humans.

Influenza viruses are enveloped viruses containing negative single-stranded RNA's which are segmented and encapsidated. The influenza virus envelope is characterized by the presence of two surface glycoproteins: hemagglutinin and neuraminidase. The influenza A and B virions are pleomorphic and are usually 80-120 nm in diameter. The influenza C virion has many distinctive properties and is thus distinguished from the closely related A and B virions.

Influenza viruses attack the respiratory tract in humans (i.e., nose, throat, and lungs). For example, infection with influenza A or B often can cause a highly contagious, acute respiratory illness. Influenza infection usually includes the following symptoms: fever, headache, tiredness (can be extreme), dry cough, sore throat, nasal congestion, and body aches.

It is estimated that millions of people in the United States—about 10% to 20% of U.S. residents—get influenza each year. The majority of this population generally recovers in one to two weeks. In some cases, however, complications can arise from an influenza infection. Those persons at highest risk for contracting complications from the flu include: persons over 50 years of age, children aged 6 to 23 months, women more than 3 months pregnant, persons living in a long-term care facility or institution, persons with chronic heart, lung, or kidney conditions, diabetes, or weakened immune system. Pneumonia, bronchitis, encephalitis, otitis media, rhinitis, and sinusitis are only a few examples of complications that result from an influenza infection. Moreover, the flu can make chronic health problems worse. For example, people with asthma may experience asthma attacks while they have the flu, and people with chronic congestive heart failure may have worsening of this condition that is triggered by the flu.

An average of about 36,000 people per year in the United States die from influenza, and 114,000 per year have to be admitted to the hospital as a result of the infection. Thus, influenza viruses have a major impact on morbidity leading to increases in hospitalization and in visits to health care providers. For example, high rates of hospitalization are often observed for subjects over 65 years of age and also for children less than 5 years of age.

Furthermore, the spread of influenza virus through a population can result in epidemics, which have considerable economic impact. High rates of mortality were observed due to influenza infection during the influenza epidemics of 1957, 1968 and 1977 (*Fields Virology*, Second Edition, Volume 1, pp. 1075-1152 (1990)). Periodically, the influenza virus causes a worldwide epidemic. For example, the influenza pandemic of 1918 reportedly caused about 20 million deaths worldwide and about 500,000 deaths in the United States (*Medical Microbiology*, Fourth Edition, University of Texas Medical Branch at Galveston (1996)).

Influenza viruses are predominantly transmitted from person to person via respiratory droplets (also known as droplet spread) that are released when coughing and/or sneezing. The influenza virus can remain suspended in the air in respiratory droplets for as long as 3 hours; but are sensitive to heat and are rapidly inactivated at temperatures above 50° C. The virus can survive for 24-48 hours on hard, non-porous surfaces (i.e., telephone receivers, computer keyboard, doorknob, kitchen countertop, toys); 8 hours on cloth, paper and tissue; and five minutes on hands (see Muir, P, "Treatment of Influenza. Essential CPE. Continuing Education from the Pharmaceutical Society of Australia," Paragon Printers, Australasia, ACT (2002)). Typical methods of transmittal include mucous membrane contact with infected airborne respiratory droplets, person-to-person contact, contact with contaminated items (i.e., tissues soiled by infected nose and throat discharges).

Transmittal of influenza virus via respiratory droplets can occur as early as one day before a person experiences influenza-related symptoms. Adults can continue to transmit the virus to others for another three to seven days after the initial appearance of symptoms. Unlike adults, children have the ability to transmit the virus for longer than seven days. Symptoms are generally presented one to four days after the virus enters the body. In certain cases, a person can be infected with the flu virus but demonstrate no symptoms. During this time, those persons can still transmit the virus to others.

Few methods are available for preventing an influenza infection and a cure has yet to be developed. Methods for preventing an influenza infection include vaccination and antiviral medications. Three antiviral drugs (amantadine, rimantadine, and oseltamivir) have been approved in the United States and are commercially available for use in preventing or treating influenza virus disease. These compounds, however, are most effective when used prophylactically, which may allow influenza viruses to develop resistance to both compounds rapidly. See U.S. Pat. Nos. 3,352,912 and 3,152,180. Other compounds reported to have activity against influenza viruses have been disclosed in U.S. Pat. Nos. 6,271, 373; 5,935,957; 5,821,243; 5,684,024; 3,592,934; 3,538,160; 3,534,084; 3,496,228; and 3,483,254.

There is a great need for new therapies for the treatment of viral diseases. Whereas there has been great progress in developing a variety of therapies for the treatment of bacterial infections, there are few viable therapies for the treatment of viruses. As described above, antiviral drugs and vaccines are primary methods used in the prevention and/or treatment of influenza infections. Ganciclovir, acyclovir and foscarnet are currently utilized for the treatment of herpes virus infections. However, these therapies can have substantial side effects based on their deleterious effects on host cell DNA replication or their effect on a limited number of viral infections. In addition, as noted above, viruses are known to develop resistance to therapies, which causes a progressive decline in efficacy.

Insofar as is known, cysteamine compounds have not been previously reported as being useful for the treatment of viral infections.

BRIEF SUMMARY OF THE INVENTION

The subject invention provides materials and methods for treating subjects diagnosed with viral infections as well as preventing the onset of viral infections. In one embodiment, the invention provides methods for the treatment of viral-related symptoms. In another embodiment, the subject invention provides methods for the prevention or delay in development of viral-related complications.

Accordingly, the present invention provides for the treatment and/or prevention of viral infections from Classes I through V viruses (see Lodish, H. et al., Molecular Cell Biology, Fourth Edition, W. H. Freeman and Company (2000)) through the administration of a cysteamine compound to a subject. More specifically, the present invention provides methods for the treatment and/or prevention of a Class I-V viral infection; the alleviation of Class I-V viral infection-related symptoms; as well as the prevention or delay in development of Class I-V viral infection-related complications.

Viral infections resulting from the following types of viruses are treated and/or prevented by administering a cysteamine compound as disclosed herein. The viruses include double-stranded DNA (dsDNA), single-stranded DNA (ssDNA), double-stranded genomic RNA (dsRNA), single-strand positive RNA, and single-strand negative RNA viruses, such as but not limited to, influenza viruses, adenoviruses; herpesviruses; human papillomaviruses; parvoviruses; reoviruses; picornaviruses; coronaviruses; flavivirus; togaviruses, orthomyxovirus; bunyaviruses; rhabdoviruses; and paramyxoviruses.

The subject invention is particularly applicable to both human and animal health, especially to animals infected by Class I-V viruses. For instance, the following, non-limiting list of viruses and resultant conditions common to non-human mammals can be treated and/or prevented using the present invention: swine circle virus 2, picomavirus; orthomyxovirus; coronavirus; togavirus; paramyxovirus; rhabdovirus; and reovirus, including any mutants thereof.

Specifically exemplified herein is the use of a cysteamine compound to treat and/or prevent an influenza virus infection. In accordance with the subject invention, administration of a cysteamine compound to a subject prior to acquiring the influenza virus can help protect the subject from influenza infection, or at least ensure that symptoms related to influenza virus disease develop to a lesser extent than would be observed in the absence of the cysteamine compound.

In another embodiment, a cysteamine compound is administered to prevent and/or delay the development of influenza-related complications in subjects who are at an increased risk of contracting those complications. For example, influenza-related complications such as encephalitis, bronchitis, tracheitis, myositis rhinitis, sinusitis, asthma, bacterial infections (i.e., streptococcus aureus bacterial infection, haemophilus influenzae bacterial infection, staphylococcal pneumonia bacterial infection), cardiac complications (i.e., atrial fibrillation, myocarditis, pericarditis), Reye's syndrome, neurologic complications (i.e., confusion, convulsions, psychosis, neuritis, Guillain-Barre syndrome, coma, transverse myelitis, encephalitis, encephalomyelitis), toxic shock syndrome, myositis, myoglobinuria, and renal failure, croup, otitis media, viral infections (i.e., viral pneumonia), pulmonary fibrosis, obliterative bronchiolitis, bronchiectasis, exacerbations of asthma, exacerbations of chronic obstructive pulmonary disease, lung abscess, empyema, pulmonary aspergillosis, myositis and myoglobinaemia, heart failure, early and late fetal deaths in pregnant women, increased perinatal mortality in pregnant women, congenital abnormalities in birth, can be reduced through consumption, according to the subject invention, of a cysteamine compound.

In another embodiment of the invention, a cysteamine compound is administered to a subject diagnosed with an influenza infection to alleviate influenza-related symptoms. A cysteamine compound can be administered alone or concurrently with other known agents that are used to treat/prevent the influenza virus disease (i.e., vaccinations, antiviral drugs) or to treat influenza-related symptoms (i.e., antitussives, mucolytics, and/or expectorants; antipyretics and analgesics; nasal decongestants).

In one embodiment, a cysteamine compound is administered alone or concurrently with other known agents that are used to treat/prevent a viral infection. Preferably, a cysteamine compound of the invention is administered to a subject prior to, during, or after a exposure to an influenza virus concurrently with known agents that are used to treat/prevent the influenza virus disease (i.e., vaccinations, antiviral drugs) or to treat influenza-related symptoms (i.e., antitussives, mucolytics, and/or expectorants; antipyretics and analgesics; nasal decongestants).

In a related embodiment, a cysteamine compound is administered alone or concurrently with other known agents that are used to treat and/or prevent an avian influenza viral (AIV) infection. According to the present invention, the cysteamine compound can be administered to a subject via injection or oral administration to treat and/or prevent an AIV infection.

Preferably, a cysteamine compound is administered alone or concurrently with other known agents useful in the treatment and/or prevention of the various subytpes of avian influenza virus. More preferably, a cysteamine compound of the invention is administered alone or concurrently with other known agents useful in the treatment and/or prevention of H5N1 AIV. A dosage of at least 0.1 mg/mL of cysteamine hydrochloride, more preferably at least 1 mg/mL of cysteamine hydrochloride, and even more preferably at least 2 mg/mL of cysteamine hydrochloride, can be administered to a subject to treat and/or prevent any of the AIV subtypes listed above, preferably an H5N1 AIV infection.

In certain preferred embodiments, the dosage of cysteamine hydrochloride administered in the treatment and/or prevention of a H5N1 AIV infection correlates to the concentration of virus present in the subject. More preferably, the dosage of cysteamine hydrochloride administered in the treatment and/or prevention of H5N1 AIV infection correlates to an initial concentration of about LD50.

In accordance with the subject invention, the daily dosage amount of a cysteamine compound administered to a subject prior to viral infection to protect the subject from viral infection can be about 10 mg to 3,000 mg. Preferably, a cysteamine compound is administered at about 50 mg to 1,500 mg per day. In a more preferred embodiment, about 200 mg to 900 mg of cysteamine hydrochloride is administered daily to a subject to prevent/treat the onset of an influenza (such as avian influenza virus, influenza A, influenza B, and influenza C or any mutants thereof) virus disease.

In accordance with the subject invention, the daily dosage amount of a cysteamine compound administered to a subject once symptoms associated with a viral infection have been presented is about 10 mg to 3,000 mg. Preferably, a cysteamine compound is administered at about 200 mg to 1,500 mg per day. In a more preferred embodiment, about 450 mg to 900 mg of cysteamine hydrochloride is administered daily to a subject to treat and/or ameliorate the severity of symptoms associated with an influenza (such as avian influenza virus, influenza A, influenza B, and influenza C or any mutants thereof) virus disease.

In accordance with the subject invention, the daily dosage amount of a cysteamine compound administered to a subject at risk for contracting complications associated with a virus infection is about 10 mg to 3,000 mg. Preferably, a cysteamine compound is administered at about 200 mg to 1,500 mg per day. In a more preferred embodiment, about 450 mg to 900 mg of cysteamine hydrochloride is administered daily to a subject to prevent and/or delay the onset of complications associated with influenza (such as avian influenza virus, influenza A, influenza B, and influenza C or any mutants thereof) virus disease.

DETAILED DISCLOSURE OF THE INVENTION

Figure 1:
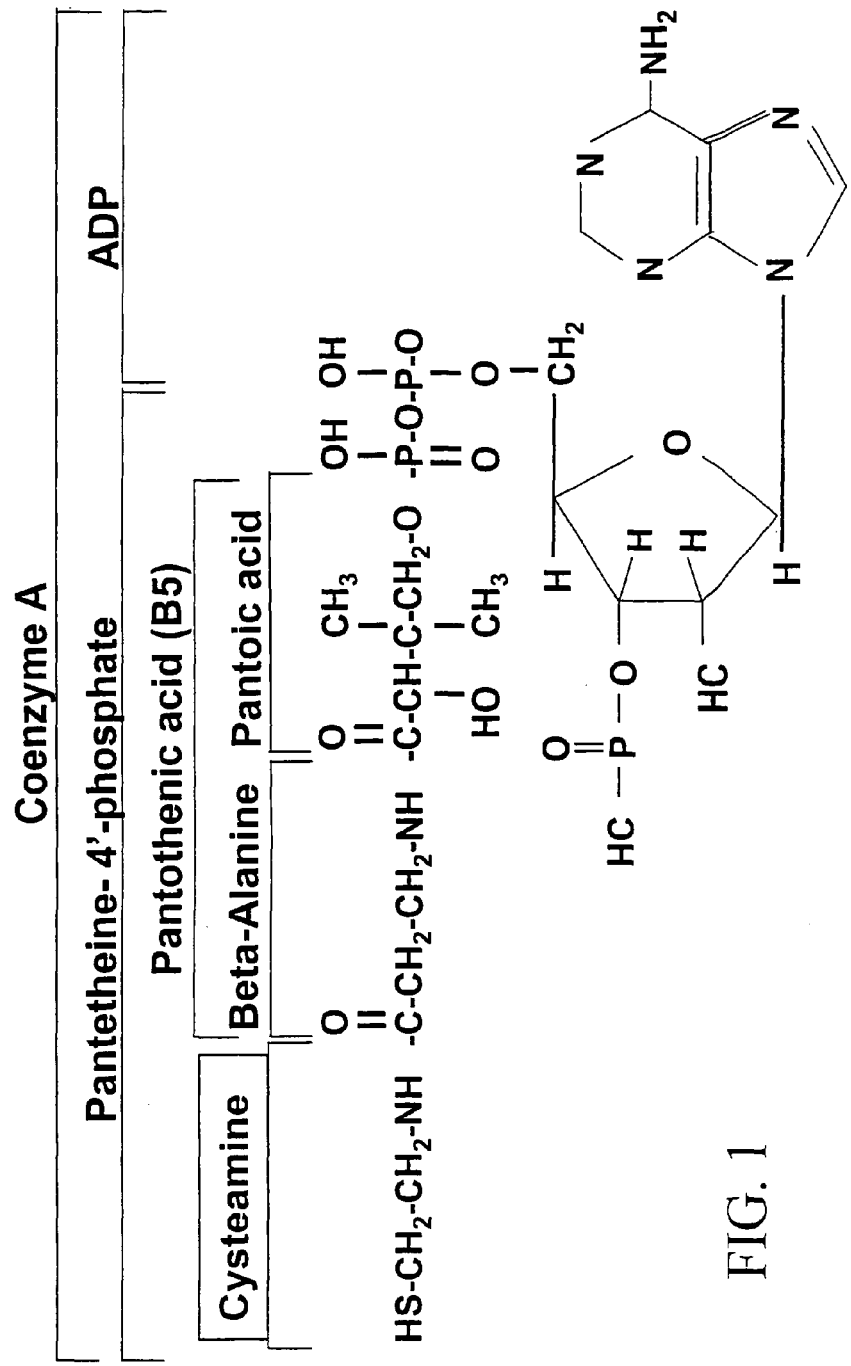
FIG. 1 shows cysteamine as a constituent of co-enzyme A.

The subject invention provides materials and methods for treating viral infections. Specifically, the subject invention provides materials methods for preventing a Class I-V viral infection; treating/ameliorating symptoms associated with Class I-V viral infections; and/or preventing/delaying the onset of complications associated with Class I-V viral infections. In preferred embodiments, the invention provides methods for preventing an influenza infection, treating/ameliorating symptoms associated with an influenza infection, as well as preventing/delaying in high-risk patients the onset of complications associated with an influenza infection.

The term "symptom(s)" as used herein, refers to common signs or indications that a subject is suffering from a specific condition or disease. For example, symptoms associated with a viral infection, as used herein, refer to common signs or indications that a subject is infected with a Class I-V virus. Influenza-related symptoms contemplated herein include, but are not limited to, fever, headache, exhaustion/fatigue, muscular aches, sore joints, irritated watering eyes, malaise, nausea and/or vomiting, shaking chills, chest pain, sneezing and respiratory symptoms (i.e., inflamed respiratory mucous membranes, substernal burning, nasal discharge, scratchy/sore throat, dry cough, loss of smell).

According to the subject invention, symptoms associated with an influenza virus infection can start within 24 to 48 hours after infection and can begin suddenly. Chills or a chilly sensation are often the first indication of influenza. Fever is common during the first few days, and the temperature may rise to 102° F. to 103° F. In many instances, subjects feel sufficiently ill to remain in bed for days; subjects often experience aches and pains throughout the body, most pronounced in the back and legs.

As used herein, the term "complication(s)" refers to a pathological process or event occurring during a disease or condition that is not an essential part of the disease or condition; where it may result from the disease/condition or from independent causes. Accordingly, the term complication(s) refers to medical/clinical problems that are observed in subjects diagnosed with a Class I-V viral infection. One complication of an influenza virus infection is that the influenza virus infection can make chronic health problems worse. For example, complications associated with a viral infection include, without limitation, encephalitis, bronchitis, tracheitis, myositis rhinitis, sinusitis, asthma, bacterial infections (i.e., streptococcus aureus bacterial infection, haemophilus influenzae bacterial infection, staphylococcal pneumonia bacterial infection), cardiac complications (i.e., atrial fibrillation, myocarditis, pericarditis), Reye's syndrome, neurologic complications (i.e., confusion, convulsions, psychosis, neuritis, Guillain-Barre syndrome, coma, transverse myelitis, encephalitis, encephalomyelitis), toxic shock syndrome, myositis, myoglobinuria, and renal failure, croup, otitis media, viral infections (i.e., viral pneumonia), pulmonary fibrosis, obliterative bronchiolitis, bronchiectasis, exacerbations of asthma, exacerbations of chronic obstructive pulmonary disease, lung abscess, empyema, pulmonary aspergillosis, myositis and myoglobinaemia, heart failure, early and late fetal deaths in pregnant women, increased perinatal mortality in pregnant women, and congenital abnormalities in birth.

The terms "influenza," "influenza virus," or "flu," as used herein, refer to an RNA virus of the Orthomyxoviridae family, including influenza A, influenza B, and influenza C, and mutants thereof. Influenza viruses contemplated herein include those viruses that have two antigenic glycosylated enzymes on their surface: neuraminidase and hemagglutinin. Various subtypes of influenza virus that can be treated using the materials and methods of the invention include, but are not limited to, the H1N1, H1N2, H2N2, H3N2, H3N8, H5N1, H5N3, H5N8, H5N9, H7N, H7N7, H9N2, and H10N7 subtypes including the following subtypes commonly known as the "Spanish Flu," "Asian Flu," "Hong Kong Flu," "Avian Flu," "Swine Flu," "Horse Flu," and "Dog Flu."

The term "subject," as used herein, describes an organism, including humans and mammals, to which treatment with the compositions according to the present invention is provided. Mammalian species that benefit from the disclosed methods of treatment include, but are not limited to, apes, chimpanzees, orangutans, humans, monkeys; and domesticated animals (i.e., pets) such as dogs, cats, mice, rats, guinea pigs, and hamsters.

"Concurrent administration" and "concurrently administering," as used herein, includes administering a compound or therapeutic method suitable for use with the methods of the invention (administration of a cysteamine compound) in the treatment of a Class I-V viral infection or for the treatment of Class I-V viral infection-related symptoms/complications.

For a subject diagnosed with an influenza infection, a cysteamine compound can be concurrently administered with vaccinations, antiviral drugs, antitussives, mucolytics, and/or expectorants; antipyretics and analgesics; nasal decongestants. By way of example, a compound can be provided in admixture with a cysteamine compound, such as in a pharmaceutical composition; or the compound and cysteamine can be provided as separate compounds, such as, for example, separate pharmaceutical compositions administered consecutively, simultaneously, or at different times. Preferably, if the cysteamine compound and the known agent (or therapeutic method) for treating/preventing influenza infection and/or treating influenza-related symptoms/complications are administered separately, they are not administered so distant in time from each other that the cysteamine compound and the known agent (method) cannot interact.

In certain embodiments of the invention, a cysteamine compound can be administered concurrently with, but not limited to, vaccination, antiviral medications such as amantadine, rimantadine, ribavirin, idoxuridine, trifluridine, vidarabine, acyclovir, ganciclovir, foscarnet, zidovudine, didanosine, zalcitabine, stavudine, famciclovir, oseltamivir, and valaciclovir (materials and/or methods used to treat an viral infection); or antitussives, mucolytics, and/or expectorants; antipyretics and analgesics; nasal decongestants (materials used to treat symptoms associated with an influenza infection).

By way of example, a compound for use with a cysteamine compound of the invention can be provided in admixture with the cysteamine compound, such as in a pharmaceutical composition. Alternatively, the compound and cysteamine can be provided as separate compounds, such as, for example, separate pharmaceutical compositions administered consecutively, simultaneously, or at different times. Preferably, if the cysteamine compound and the known agent (or therapeutic method) for treating/preventing influenza infection and/or treating influenza-related symptoms/complications are administered separately, they are not administered so distant in time from each other that the cysteamine compound and the known agent (method) cannot interact.

As used herein, reference to a "cysteamine compound" includes cysteamine, the various cysteamine salts, which include pharmaceutically acceptable salts of a cysteamine compound, as well as prodrugs of cysteamine that can, for example, be readily metabolized in the body to produce cysteamine. Also included within the scope of the subject invention are analogs, derivatives, conjugates, and metabolic precursors (such as cysteine, cystamine, pantethine, and the like) as well as metabolites (such as taurine, hypotaurine, and the like) of cysteamine, which have the ability as described herein to treat and/or prevent stress and stress-related symptoms/complications by lowering cortisol levels as well as augment immune activity. Various analogs, derivatives, conjugates, and metabolites of cysteamine are well known and readily used by those skilled in the art and include, for example, compounds, compositions and methods of delivery as set forth in U.S. Pat. Nos. 6,521,266; 6,468,522; 5,714,519; and 5,554,655.

As contemplated herein, a cysteamine compound includes pantothenic acid. Pantothenic acid is a naturally occurring vitamin that is converted in mammals to coenzyme A, a substance vital to many physiological reactions. Cysteamine is a component of coenzyme A, and increasing coenzyme A levels results in increased levels of circulating cysteamine. Alkali metal salts, such as magnesium phosphate tribasic and magnesium sulphite (Epsom salts), enhance formation of coenzyme A. Furthermore, breakdown of coenzyme A to cysteamine is enhanced by the presence of a reducing agent, such as citric acid. Thus, the combination of pantothenic acid and alkali metal salts results in increased coenzyme A production and, concomitantly, cysteamine.

The term "pharmaceutically acceptable salt," as used herein, refers to any salt of a cysteamine compound that is pharmaceutically acceptable and does not greatly reduce or inhibit the activity of the cysteamine compound. Suitable examples include acid addition salts, with an organic or inorganic acid such as acetate, tartrate, trifluoroacetate, lactate, maleate, fumarate, citrate, methane, sulfonate, sulfate, phosphate, nitrate, or chloride.

Figure 2:
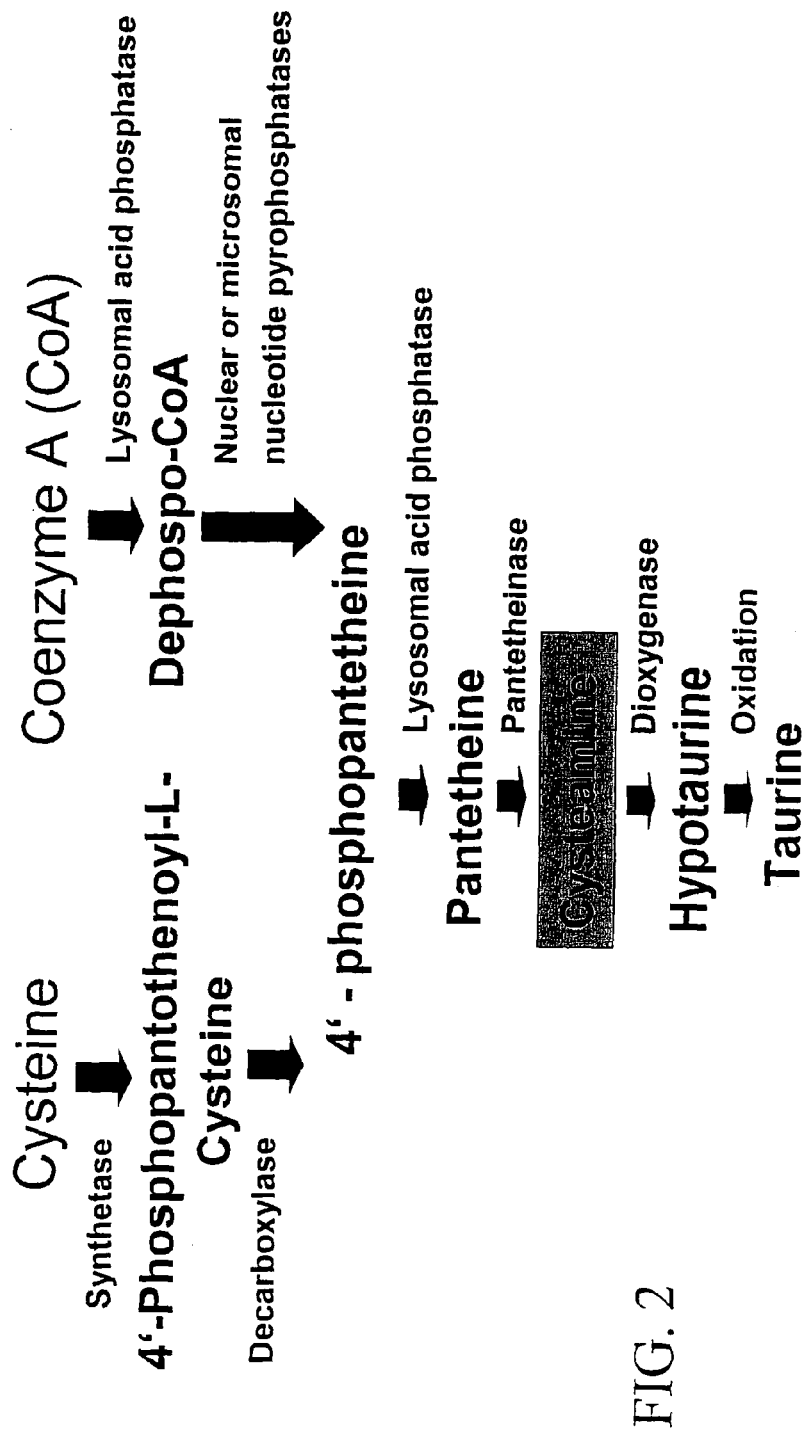
FIG. 2 shows a metabolic pathway of cysteamine.

Accordingly, in one embodiment of the subject invention, the advantages of cysteamine, as set forth herein, can be achieved by promoting the endogenous production of cysteamine through natural metabolic process such as through the action of co-enzyme A or as a precursor and/or metabolite of cysteine (see FIGS. 1 and 2). This can be achieved by, for example, the administration of pantothenic acid.

The term "effective amount," as used herein, refers to the amount necessary to elicit the desired biological response. In accordance with the subject invention, the effective amount of a cysteamine compound is the amount necessary to treat/prevent a Class I-V viral infection; treat/ameliorate symptoms associated with Class I-V viral infections; and/or prevent/delay/ameliorate the onset of complications associated with Class I-V viral infections. In a preferred embodiment, the effective amount of a cysteamine compound is the amount necessary to treat/prevent an influenza infection; treat/ameliorate symptoms associated with influenza infection; and/or prevent/delay/ameliorate the onset of complications in patients with increased risk for contracting complications associated with influenza infection. The amelioration in symptom and/or complication severity may be a 5%, 10%, 15%, 20%, 25% 30%, 35%, 40%, 45%, 50%, 55%, 60%, 65%, 70%, 75%, 80%, 85%, 90%, 95%, 98% or 99% decrease in severity.

As used herein, the term "Class I-V viruses" refers to the different classes of virus identified by genome composition and strategy for mRNA synthesis, as described in Lodish, H. et al., *Molecular Cell Biology*, Fourth Edition, W. H. Freeman and Company (2000). Class I-V viruses are identified as follows:

Class I viruses contain a single molecule of double-stranded DNA;

Class II viruses contain a single molecule of single-stranded DNA;

Class III viruses contain double-stranded genomic RNA;

Class IV viruses contain a single strand of viral MRNA (also known as a positive/plus strand of genomic RNA), wherein the viral mRNA encodes proteins and is infectious by itself; and Class V viruses contain a single strand of an RNA sequence that is complimentary to the genomic viral mRNA (also known as a negative/minus strand of genomic RNA), wherein the genomic RNA acts as a template for synthesis of mRNA but does not itself encode proteins.

The present invention provides materials and methods for treating and/or preventing a Class I-V viral infection through the administration of a cysteamine compound to a subject. Viral infections resulting from the following types of viruses are treated and/or prevented by administering a cysteamine compound as disclosed herein. The viruses include double-stranded DNA (dsDNA), single-stranded DNA (ssDNA), double-stranded genomic RNA (dsRNA), single-strand positive RNA, and single-strand negative RNA viruses. Contemplated viruses that can be treated in accordance with the subject invention include, but are not limited to, arboviruses (included but not limited to, dengue virus, yellow fever, and the like); adenoviruses (included but not limited to acute respiratory illness, pneumonia, conjunctivitis, gastroenteritis, pharyngitis, acute haemorrhagic cystitis, African swine fever, porcine circovirus, porcine adenoviruses A, B, and C); herpesviruses (included but not limited to herpes simplex virus, varicella zoster virus (chicken pox and shingles), Epstein-Barr virus); human papillomaviruses (included but not limited to HPV types 1-65); parvoviruses (included but not limited to parvovirus B19, canine parvovirus); reoviruses (included but not limited to orbivirus, rotavirus, aquareovirus, coltivirus); picornaviruses (included but not limited to enterovirus, rhinovirus, hepatovirus); coronaviruses (included but not limited to coronavirus and torovirus); flavivirus (included but not limited to petsivirus, hepatitis C-like viruses); togaviruses (included but not limited to alphavirus and rubivirus), orthomyxovirus (included but not limited to influenza A, B, and C viruses, avian influenza virus, Thogoto virus); bunyaviruses (included but not limited to Hantavirus, Nairovirus, phlebovirus); rhabdoviruses (included but not limited to rabies virus, ephemerovirus, vesiculovirus); and paramyxoviruses (included but not limited to measles virus and mumps virus).

The present invention is particularly applicable to non-human subject health, especially to non-human subjects infected with a Class I-V virus. For instance, the following, non-limited list of viruses and resultant conditions common in non-human subjects can be treated and/or prevented using the present invention: picornavirus (avian encephalomyelitis, duck hepatitis and calicivirus (cat) infections); orthomyxovirus (fowl plague and avian influenza (H5N1)); coronavirus (infectious bronchitis and coronaviral enteritis in poultry and canine corona virus in dogs); togavirus (pheasant encephalitis); paramyxovirus (Newcastle's Disease in poultry and canine distemper and parainfluenza in dogs); rhabdovirus (rabies and viral hemorrhagic disease in fish); and reovirus (poultry infectious bursal disease).

With regard to human subjects, the present invention is particularly applicable to the treatment and/or prevention of influenza virus infections, especially avian influenza virus infections. According to the subject invention, a cysteamine compound is useful in the treatment and/or prevention of various avian influenza strains, including viruses of subtype H1N1, H1N2, H2N2, H3N2, H3N8, H5N1, H5N2, H5N3, H5N8, H5N9, H7N1, H7N2, H7N3, H7N4, H7N7, H9N2, and H10N7. In one embodiment of the invention, cysteamine hydrochloride is administered to subjects (either human or animal) in order to treat and/or prevent a H5N1 avian influenza virus infection. The cysteamine hydrochloride can be administered alone or concurrently with other known agents known to be effective in treating and/or preventing an influenza infection.

In a related embodiment, a cysteamine compound (such as cysteamine hydrochloride) is administered alone or concurrently with other known agents that are used to treat and/or prevent an avian influenza viral (AIV) infection. The cysteamine compound can be administered to a subject via injection or oral administration.

Preferably, a dosage of at least 0.1 mg/mL of cysteamine hydrochloride, more preferably at least 1 mg/mL of cysteamine hydrochloride, and even more preferably at least 2 mg/mL of cysteamine hydrochloride, can be administered to a subject to treat and/or prevent a H5N 1 AIV infection.

In certain preferred embodiments, the dosage of cysteamine hydrochloride administered in the treatment and/or prevention of an AIV infection (including viruses of subtype H1N1, H1N2, H2N2, H3N2, H3N8, H5N1, H5N2, H5N3, H5N8, H5N9, H7N1, H7N2, H7N3, H7N4, H7N7, H9N2, and H10N7) correlates to the concentration of virus present in the subject. More preferably, the dosage of cysteamine hydrochloride administered in the treatment and/or prevention of a H5N1 AIV infection correlates to a concentration of about LD50 of virus present in the subject.

The compositions of the invention can be used in a variety of routes of administration, including, for example, orally-administrable forms such as tablets, capsules or the like, or via parenteral, intravenous, intramuscular, transdermal, buccal, subcutaneous, suppository, or other route. Such compositions are referred to herein generically as "pharmaceutical compositions." Typically, they can be in unit dosage form, namely, in physically discrete units suitable as unitary dosages for human consumption, each unit containing a predetermined quantity of active ingredient calculated to produce the desired therapeutic effect in association with one or more pharmaceutically acceptable other ingredients, i.e., diluent or carrier.

The cysteamine compounds of the subject invention can be formulated according to known methods for preparing pharmaceutically useful compositions. Formulations are described in a number of sources, which are well known and readily available to those skilled in the art. For example, *Remington's Pharmaceutical Science* (Martin EW [1995] Easton Pa., Mack Publishing Company, $19^{th}$ ed.) describes formulations that can be used in connection with the subject invention. Formulations suitable for parenteral administration include, for example, aqueous sterile injection solutions, which may contain antioxidants, buffers, bacteriostats, and solutes, which render the formulation isotonic with the blood of the intended recipient; and aqueous and nonaqueous sterile suspensions, which may include suspending agents and thickening agents. The formulations may be presented in unit-dose or multi-dose containers, for example sealed ampoules and vials, and may be stored in a freeze dried (lyophilized) condition requiring only the condition of the sterile liquid carrier, for example, water for injections, prior to use. Extemporaneous injection solutions and suspensions may be prepared from sterile powder, granules, tablets, etc. It should be understood that in addition to the ingredients particularly mentioned above, the formulations of the subject invention can include other agents conventional in the art having regard to the type of formulation in question.

The formulations comprising a cysteamine compound include those suitable for oral, rectal, nasal, topical (including buccal and sublingual), vaginal, parenteral (including subcutaneous, intramuscular, intravenous, intradermal, intrathecal and epidural) administration as well as administration to the eye. The formulations may conveniently be presented in unit dosage form and may be prepared by any of the methods well known in the art of pharmacy. Such methods include the step of bringing into association the cysteamine compound with the carrier which constitutes one or more accessory ingredients. In general the formulations are prepared by uniformly and intimately bringing into association the cysteamine compound with liquid carriers or finely divided solid carriers or both, and then, if necessary, shaping the product. In certain embodiments, the cysteamine compound can be provided in a formulation for use in a skin patch.

Administration of a cysteamine compound, in accordance with the subject invention, can be accomplished by any suitable method and technique presently or prospectively known to those skilled in the art. In a preferred embodiment, a cysteamine compound is formulated in a patentable and easily consumed oral formulation such as a pill, lozenge, tablet, gum, beverage, etc. The consumption is then taken at, prior to, or after, experiencing a stressful event and/or when needed to augment immune activity (i.e., after diagnosis with an influenza infection).

In accordance with the invention, compositions comprising, as an active ingredient, an effective amount of the cysteamine and one or more non-toxic, pharmaceutically acceptable carrier or diluent. Examples of such carriers for use in the invention include ethanol, dimethyl sulfoxide, glycerol, silica, alumina, starch, sorbitol, inosital, xylitol, D-xylose, manniol, powdered cellulose, microcrystalline cellulose, talc, colloidal silicon dioxide, calcium carbonate, magnesium cabonate, calcium phosphate, calcium aluminium silicate, aluminium hydroxide, sodium starch phosphate, lecithin, and equivalent carriers and diluents.

To provide for the administration of such dosages for the desired therapeutic treatment, compositions of the invention will typically comprise between about 0.1% and 95%, of the total composition including carrier or diluent. The dosage used can be varied based upon the age, weight, health, or the gender of the individual to be treated.

In one embodiment, the dosage of cysteamine administered to a patient to elicit a desired response is about 10 mg to about 3,000 mg per day. The desired response can include (1) prevention of Class I-V viral infections; preferably influenza infection; (2) a reduction in the severity, duration, or intensity of symptoms associated with Class I-V infections, preferably symptoms associated with influenza infection; and (3) prevention, delay, or reduction in the severity, duration, or intensity of complications related to a Class I-V viral infections, complications related to influenza infections. Preferably, cysteamine hydrochloride is administered daily at about 50 mg to 1,000 mg to elicit a desired response. In a more preferred embodiment, the dosage of cysteamine hydrochloride administered to a patient to elicit a desired response is about 200 mg to 900 mg per day.

Following are examples that illustrate procedures for practicing the invention. These examples should not be construed as limiting. All percentages are by weight and all solvent mixture proportions are by volume unless otherwise noted.

EXAMPLE 1

Treatment of Influenza-Related Symptoms

A male subject infected with an influenza virus, demonstrating symptoms (nasal discharge, fever, exhaustion) associated with an influenza infection, was initially treated with over-the-counter nasal decongestant and mucolytic medications. The over-the-counter medications were ineffective in treating the influenza-related symptoms within 24 hours.

After the over-the-counter medications proved ineffective, the subject was administered orally a dose of about 700 mg of cysteamine hydrochloride. Within 24 hours, symptoms associated with the influenza infection had disappeared. The subject expressed general feelings of health.

EXAMPLE 2

Study of Antiviral Activity of Cysteamine against H5N1 Avian Influenza Virus: In-vitro and In-vivo Studies Using Oseltamivir Phosphate as Control According to one embodiment of the invention, cysteamine demonstrates antiviral activity against H5N1 avian influenza virus. The subject matter of the present invention is particularly advantageous due to its unexpected results with avian influenza virus. For example, as described below, cyatemine is particularly efficacious in treating H5N1 avian influenza virus, more so than even oseltamivir phosphate (whose generic name is TAMIFLU®), which is a licensed drug against avian influenza virus.

Materials and Method

Cysteamine (hereinafter referred to as "TG21"; comprising 99% cysteamine) was supplied by Omega Bio-Pharma (H.K.) Limited. Embryonated eggs from specific-pathogen-free (SPF) hens (Beijing, China) were used in this experiment. H5N1 avian influenza viruses CV strain was isolated from infected chickens. Roman chickens were purchased from Hebei without immunization with avian influenza vaccine. TAMIFLU® (Roche (China) Ltd., Shanghai, China) was used as described herein.

Evaluation of TG21 Toxicity in Embryonated Hen Eggs

One gram of TG21 was dissolved in 10 mL (1:10) 0.01 mol/L, in pH7.2 PBS (1:10, 10 mg/mL), and then diluted in 2-fold serials from 1:10 to 1:5120. The diluted drug (test group) or PBS buffer (control group) was injected into chorio allantoic cavities of 10-day-old embryonated hen eggs, 5 eggs each dilution. The eggs were hatched at 37° C. and monitored twice a day for 5 days to observe embryo survival and to calculate LD50 (50% Lethal Dose of virus).

Evaluation of EID50 of H5N1 Avian Influenza in Embryonated Hen Eggs

Original stock of avian influenza viruses CV strain was diluted 10-fold series with 0.01 M pH7.2 PBS from $10^{-1}$ to $10^{-10}$. The 0.2 mL diluted virus (test group) or PBS buffer (control group) was inoculated into chorio allantoic cavities of 10-day-old embryonated hen eggs, 5 eggs each dilution. The eggs were hatched at 37° C. and monitored twice a day for 5 days to observe embryo survival. EID50 (50% egg infective dose) was calculated based on Reed-Muench Method.

Evaluation of TG21 Antiviral Effect on Avian Influenza in Embrvonated Hen Eggs.

One gram of TG21 was dissolved in 10 mL 0.01 mol/L, in pH7.2 PBS (1:10, 100 mg/mL), and then diluted in 2-fold serials from 1:10 to 1:5120. The diluted TG 21 solution was incubated with same volume of 10 or 100 times EID50 H5N1 avian influenza viruses CV strain at room temperature for 30, 60 and 120 minutes, respectively, and then the 0.2 mL virus-drug mixture solution was inoculated into chorio allantoic cavities of 10-day-old embryonated eggs from SPF hens. All of the embryonated eggs were hatched at 37° C. and monitored twice a day for 5 days to observe embryo survival. The IC50 was calculated.

As a positive control, the antiviral effect of TAMIFLU® on avian influenza virus was evaluated under 100 times EID50.

Evaluation of Avian Influenza Viruses LD50 in Chicken.

The original stock of avian influenza viruses CV strain was diluted 10-fold series with 0.01 M pH7.2 PBS from $10^{-1}$ to $10^{-9}$, and then was used to infect the chickens by nasal dropping, 10 heads each dilution. The animals were monitored twice a day for 7 days to observe survival. The LD50 of avian influenza viruses to chicken was calculated according to animal survival.

Evaluation of TG21 Efficiency against Avian Influenza in Chicken.

4 to 6-week-old Roman chickens were administered TG21 through drinking water, with dosages of 40, 20, 10 mg TG21/head.day$^{-1}$ high for three days, then the chickens were challenged with 2.5, 25, 250 times EID50 by nasal dropping, once a day for three days. The animals continued to accept treatment with same doses of TG21 for five days after challenge. The chickens were monitored twice a day for 7 days. A negative control without treatment was carried out in parallel.

Animal survival was recorded and the efficiency of TG21 drug was evaluated in accordance to the following formula:

Efficiency=(death date in control group-death rate of treatment group)/(death rate of control group)× 100%.

Results

1. Toxicity 120 hours after TG21 was inoculated into embryonated eggs, some toxicity was detected at a high doses ranging from about 100 mg/mL (1:10 dilution) to 25 mg/mL (1:40). The LD50 of TG21 to embryonated hen eggs was 32.1 mg/mL. No side-effect was found when dosed below 12.5 mg/mL (1:80).

2. EID50 of H5N1 Avian Influenza in Embryonated Hen Eggs, and LD50 in Chicken.

When an original stock of virus was diluted more than $10^9$ times (concentration $10^{-9}$), embryonated eggs survived. According to the Reed-Muench Method, EID50 of H5N1 avian influenza in embryonated hen eggs was calculated as $10^{-8.17}$. When virus stock was diluted to $10^{-8}$ or below, the tested virus was not lethiferous. The LD50 of H5N1 avian influenza in chicken was $10^{-5.41}/0.2$ mL.

3. Antiviral Effect of TG21 on H5N1 Avian Influenza Viruses in Embryonated Hen Eggs.

Prior to inoculation into embryonated hen eggs, the H5N1 avian influenza viruses were treated with different dilutions of TG21 for 30, 60, and 120 minutes. The IC50s of TG21 against H5N1 avian influenza virus were 15.6, 14.9, and 6.8 mg/mL, respectively, with treatment times of 30, 60, and 120 minutes under 10 times EID50 viral challenge dose. The IC50s were 17.5 and 16.1 mg/mL, respectively, when the virus was treated with TG21 for 30 and 120 minutes prior to inoculation under virus doses of 10 times EID50 (see Table 1 below).

In a positive control group treated with TAMIFLU®, the IC50s of TAMIFLU® against H5N1 avian influenza in embryonated hen eggs were 25.1 and 19.4 mg/Ml, respectively, with 30 and 120 minutes treatment times prior to inoculation under a virus dose of 100 times EID50. In a negative control group (no drug administered), all embryonated hen eggs died.

Efficiency of TG21 against H5N1 Avian Influenza Viruses in Chickens.

Four to six-week-old chickens were administered with 10-40 mg/head.day$^{-1}$ TG21 through drinking water for three days before and for five days after challenge with high virus dosage (250×LD50), mediate virus dosage (25×LD50), and low virus dosage (2.5×LD50) of infectious H5N1 avian influenza viruses. The results of TG21's antiviral effect on H5N1 avian influenza virus in the chickens are showed in Table 2 below. All of the tested chickens died within three days under 250 times LD50 viral infectious dosages, including the animals in the TAMIFLU® control group. This may due to too high A dosage of viral infection such that no medicinal treatment, including TAMIFLU®, can provide effective protection against the viral infection.

The protection of TG21 against H5N1 avian influenza virus in chickens in dosages of 40, 20, 10 mg/head.day$^{-1}$ was 100%, 62.5%, and 87.5%, respectively, under 2.5 times LD50 viral infectious doses, and 70%, 80%, and 50%, respectively, under 25 times LD50 viral infectious doses. The statistical difference of efficiency of TG21 and of the negative control (no drug) was extremely significant (all p volume <0.01 by Chi-square test). The efficiency of TAMIFLU® (5 mg/head.day$^{-1}$) was 50% under 25 times LD50 viral challenge doses. No significant difference between IC50 of TG21 (10 mg/head.day$^{-1}$) and TAMIFLU® (5 mg/head.day$^{-1}$) was found (P.>0.05) under 25 times LD50 viral challenge doses (Table 2).

TABLE 2

Antiviral effect of TG21 on H5N1 avian influenza virus in Chicken

| Drug and Dose | | Viral infectious dose | | |
|---|---|---|---|---|
| | | 250 LD50 | 25 LD50 | 2.5 LD50 |
| TG 21 | 40 mg/mL | 0% (0/10$^a$) | 70% (7/10)** | 100% (10/10)** |
| | 20 mg/mL | 0% (0/10) | 80% (8/10)** | 62.5% (7/10)** |
| | 10 mg/mL | 0% (0/10) | 50% (5/10)** | 87.5% (9/10)** |

TABLE 1

Antiviral effect of TG21 on H5N1 AIV in embryonated hen eggs

| | | 10 EID50$^a$ | | | 100 EID50 | |
|---|---|---|---|---|---|---|
| | | 30 Mins$^b$ | 60 Mins | 120 Mins | 30 Mins | 120 Mins |
| | | Embryo survival (%) | | | | |
| TG21 Dilutions | 1:10$^c$ | 100% (16/16$^d$) | 100% (17/17) | 100% (21/21) | 100% (16/16) | 100% (16/16) |
| | 1:20 | 100% (11/11) | 100% (12/12) | 100% (16/16) | 100% (11/11) | 100% (11/11) |
| | 1:40 | 75% (6/8) | 77.8% (7/9) | 100% (11/11) | 100% (6/6) | 100% (6/6) |
| | 1:80 | 37.5% 3/8) | 40% (4/10) | 66.7% (6/9) | 0% (0/5) | 20% (1/5) |
| | 1:160 | 10% (1/10) | 27% (3/11) | 36.4% (4/11) | 0% (0/10) | 0% (0/9) |
| | 1:320 | 0% (0/14) | 0% (0/13) | 21% (3/14) | 0% (0/15) | 0% (0/14) |
| | 1:640 | 0% (0/19) | 0% (0/18) | 13% (2/16) | 0% 0/20) | 0% (0/19) |
| | 1:1280 | 0% (0/24) | 0% (0/23) | 0% (0/19) | 0% (0/25) | 0% (0/24) |
| | 1:2560 | 0% (0/29) | 0% (0/28) | 0% (0/24) | 0% (0/30) | 0% (0/29) |
| | | IC 50$^e$ | | | | |
| IC50 (mg/mL) | | 15.6 | 14.9 | 6.8 | 17.5 | 16.1 |

Note:
Mins = minutes;
$^a$EID50: drug dose for 50% egg infection;
$^b$reaction time of drug-virus prior inoculation;
$^c$drug initialization concentration is 100 mg/mL;
$^d$survival/total;
$^e$IC50: the drug concentration required to survive 50% embryo.

TABLE 2-continued

Antiviral effect of TG21 on H5N1
avian influenza virus in Chicken

| Drug and Dose | Viral infectious dose | | |
|---|---|---|---|
| | 250 LD50 | 25 LD50 | 2.5 LD50 |
| Tamiflu (5.4 mg/mL) | 0% (0/10) | 50% (5/10)** | N/A |
| Negative control | 0% (0/10) | 0% (0/10) | 20% (2/10) |

Note:
**P < 0.01 compare with control group by Chi-square test;
[a]survival/total Summary Ten-day-old embryonated eggs from SPF (specific-pathogen-free) hens and four to six-week-old chickens were used in this study to test antiviral effect of TG21 on H5N1 avian influenza viruses CV strain. The LD50 (50% Lethal Dose) of virus to chicken, EID50 (50% egg infective dose) of virus to embryonated eggs, and LD50 of TG21 to embryonated eggs were determined firstly. For the in vitro studies, the viruses were pre-incubated with different concentration TG 21 for 30-120 minutes, respectively, and then 5 inoculated into embryonated eggs to observe survival of the embryo. The IC50 (the drug concentration required to survive 50% embryo) of TG21 was calculated. For the in vivo studies, the chickens were administered with TG21 in high, mediate and low doses of AIV through drinking water for three days before and five days after challenged with viruses. Animal survival was recorded and the efficiency of drug was evaluated. A positive control (TAMIFLU®) and a negative control (no drug) were carried out in in parallel studies. Results showed that, (1) the IC50s of TG21 against H5N1 avian influenza viruses in embryonated hen eggs were 15.6, 14.9, 6.8 mg/mL, respectively, when 10 times EID50 viruses were treated with TG21 for 30, 60, 120 minutes prior to inoculation, 17.5 and 16.1 mg/mL, respectively, when 100 times EID50 viruses was treated with the drug for 30 and 120 minutes prior to inoculation. The IC50s of TAMIFLU® against H5N 1 avian influenza virus in embryonated hen eggs were 25.1 and 19.4 mg/mL, respectively, when the 100 times EID50 viruses were incubated with TAMIFLU® for 30 and 60 minutes prior to inoculation; and (2) the efficiency of TG21 in a doses of 40, 20, 10 mg/head.day$^{-1}$ against H5N1 avian influenza virus induced mortality in chickens was 100%, 62.5%, and 87.5%, respectively, under 2.5 times LD50 viral challenge dose, and 70%, 80% and 50% under 25 times LD50 viral challenge dose, while the efficiency of TAMIFLU® (5 mg/head.day$^{-1}$) was 50%. These results suggest cysteamine has a strong antiviral activity against H5N1 avian influenza virus, where it can provide similar or even better protection against H5N1 avian influenza virus as compared to current licensed drugs against avian influenza, such as TAMILFLU®.

EXAMPLE 3

Antiviral Activity of Cysteamine Against H5N1 Avian Influenza Virus in Mice Materials and Method Cysteamine (hereinafter referred to as "TG21"; comprising 99% cysteamine) was supplied by Omega Bio-Pharma (H.K.) Limited. H5N1 avian influenza virus, WV strain, was isolated from infected chickens. TAMIFLU® (Roche (China) Ltd., Shanghai, China) was used as described herein.

Evaluation of 50% Lethal Dose of H5N1 Avian Influenza Virus in Mice (mLD50)

H5N1 avian influenza (WV strain) stock solution was initially diluted 1:5 and then diluted with PBS in four-fold series for 5 dilutions (1:5 to 1:1280). Six to eight-week old female mice were anesthetized by intramuscularly injection 100 μL of 1% sodium barbiturate and then inoculated by dropping 50 μL diluted H5N1 avian influenza virus WV strain into each mouse's nasal cavity (n=10 mice for each dilution). Animals were monitored daily for 14 days and mLD50 was calculated based on the death of mice with the Reed-Muench Method. The results indicate that the survival of the mice were 0% in the 1:5 virus dilution group, 10% in the 1:20 virus dilution group, 25% in the 1:80 virus dilution group, 80% in the 1:320 virus dilution group, and 90% in the 1:1280 virus dilution group. The mLD50 of H5N1 avian influenza (WV strain) was $10^{-2.1509}$/0.05 mL or 1:141.5 dilution/0.05 mL.

Theraipeutic Role of Cysteamine in Mice Infected with Avian Influenza Virus

Fifty female mice (6-8 weeks old) were allotted into three treatment groups (T1, T2, and T3), one negative (untreated) control group, and one positive (TAMIFLU®) control group, with 10 mice in each group. After being anesthetized via intramuscular injection of 100 μL 1% sodium barbiturate, all of the mice were inoculated intranasally with 10 times mLD50 H5N1 avian influenza virus in 50 μL PBS. Within one hour after infection, the animals was treated for 12 days by oral gavage administration with TG21 at a daily dose of 4.8, 2.4, 1.2 mg per mouse in T1-T3 treatment groups respectively, TAMILFLU® 0.3 mg per mouse daily in the positive control group and same volume of PBS in the negative group.

Mice were observed twice a day for 14 days for clinical signs of infection and for survival. The protection rate of TG21 against H5N1 avian influenza was calculated and the significant differences between the groups were compared by Chi-square test. For example, the equation for identifying the protection rate (%)=(death date in control group-death rate of treatment group)/(death rate of control group)×100%. Results showed that the protection were 50%, 70% and 10% in TG21 treatment of T1 group (4.8 mg/mouse.day$^{-1}$), T2 group (2.4 mg/mouse.day$^{-1}$), and T3 group (1.2 mg/mouse.day$^{-1}$), respectively; with a 0% protection rate in the negative control group and a 60% protection rate in the positive (TAMIFLU®) control group. The protection rate of TG21 in the T1 group (P<0.05), T2 group (P<0.01), and T3 group (P<0.05) differed significantly from that in the negative control group. These results indicate that TG21 has a strong antiviral activity against H5N1 avian influenza virus as an ideal drug in the treatment of avian influenza viral infections.

All patents, patent applications, and publications referred to or cited herein are incorporated by reference in their entirety, including all figures and tables, to the extent they are not inconsistent with the explicit teachings of this specification.

It should be understood that the examples and embodiments described herein are for illustrative purposes only and that various modifications or changes in light thereof will be suggested to persons skilled in the art and are to be included within the spirit and purview of this application.

We claim:

1. A method for treating a viral influenza infection, wherein said method comprises diagnosing a subject with the viral influenza infection; and administering to the subject an effective amount of cysteamine or a salt thereof.

2. The method, according to claim 1, wherein the subject is infected with at least one of the group consisting of influenza virus subtype H1N1, H1N2, H2N2, H3N2, H3N8, H5N1, H5N2, H5N3, H5N8, H5N9, H7N1, H7N2, H7N3, H7N4, H7N7, H9N2, and H10N7.

3. The method, according to claim 2, wherein the influenza virus subtype(s) is selected from the group consisting of avian influenza viruses, Spanish influenza viruses, Asian influenza viruses, Hong Kong influenza viruses, swine influenza viruses, equine influenza viruses, canine influenza viruses, and influenza A, B, and C viruses.

4. The method according to claim 1, which comprises administering at least 0.1 mg of the cysteamine, or salt thereof, to the subject daily.

5. The method, according to claim 4, which comprises administering between 2 mg to 3,000 mg of the cysteamine, or salt thereof, daily.

6. The method, according to claim 1, wherein said cysteamine salt is cysteamine hydrochloride.

7. The method, according to claim 1, wherein said cysteamine, or salt thereof, is taken orally, parenterally, intravenously, intramuscularly, transdermally, via buccal route, subcutaneously, or via suppository.

8. A method for reducing the severity, intensity, or duration of symptoms associated with a viral influenza infection, wherein said method comprises diagnosing a subject with the viral influenza infection; and administering to the subject an effective amount of cysteamine, or salt thereof.

9. The method, according to claim 8, wherein the subject is infected with at least one of the group consisting of influenza virus subtype H1N1, H1N2, H2N2, H3N2, H3N8, H5N1, H5N2, H5N3, H5N8, H5N9, H7N1, H7N2, H7N3, H7N4, H7N7, H9N2, and H10N7.

10. The method, according to claim 9, wherein the influenza virus subtype(s) is selected from the group consisting of avian influenza viruses, Spanish influenza viruses, Asian influenza viruses, Hong Kong influenza viruses, swine influenza viruses, equine influenza viruses, canine influenza viruses, and influenza A, B, and C viruses.

11. The method, according to claim 8, which comprises administering at least 0.1 mg of the cysteamine, or salt thereof, to the subject daily.

12. The method, according to claim 11, which comprises administering between 2 mg to 3,000 mg of the cysteamine, or salt thereof, daily.

13. The method according to claim 8, wherein the cysteamine salt is cysteamine hydrochloride.

14. The method, according to claim 8, wherein said cysteamine, or salt thereof, is taken orally, parenterally, intravenously, intramuscularly, transdermally, via buccal route, subcutaneously, or via suppository.

* * * * *

UNITED STATES PATENT AND TRADEMARK OFFICE
CERTIFICATE OF CORRECTION

PATENT NO. : 8,415,398 B2  
APPLICATION NO. : 11/605551  
DATED : April 9, 2013  
INVENTOR(S) : Hao Yi Liang et al.

Page 1 of 1

It is certified that error appears in the above-identified patent and that said Letters Patent is hereby corrected as shown below:

In the Specification

Column 1,  
Line 33, "bimaviridae," should read --birnaviridae,--.  
Line 35, "picomaviridae," should read --picornaviridae,--.  
Line 36, "bomaviridae," should read --bornaviridae,--.

Column 3,  
Line 49, "picomaviruses;" should read --picornaviruses;--.  
Line 57, "picomavirus;" should read --picornavirus;--.

Column 6,  
Line 45, "H5N9, H7N, H7N7," should read --H5N9, H7N1, H7N2, H7N3, H7N4, H7N7,--.

Column 8,  
Line 45, "viral MRNA" should read --viral mRNA--.

Column 9,  
Line 60, "H5N 1" should read --H5N1--.

Signed and Sealed this  
Eleventh Day of February, 2014

Michelle K. Lee  
*Deputy Director of the United States Patent and Trademark Office*